United States Patent
Aberg et al.

(10) Patent No.: US 9,808,419 B2
(45) Date of Patent: Nov. 7, 2017

(54) MEDICINAL TREATMENT OF DERMAL INFECTIOUS DISORDERS WITH NORKETOTIFEN

(71) Applicant: BRIDGE PHARMA, INC., Sarasota, FL (US)

(72) Inventors: A. K. Gunnar Aberg, Sarasota, FL (US); Vincent B. Ciofalo, Branford, CT (US)

(73) Assignee: BRIDGE PHARMA, INC, Sarasota, FL (US)

( * ) Notice: Subject to any disclaimer, the term of this patent is extended or adjusted under 35 U.S.C. 154(b) by 0 days.

(21) Appl. No.: 15/071,546

(22) Filed: Mar. 16, 2016

(65) Prior Publication Data

US 2016/0193143 A1   Jul. 7, 2016

Related U.S. Application Data

(63) Continuation of application No. 14/437,534, filed as application No. PCT/US2013/067177 on Oct. 29, 2013, now abandoned, which is a continuation-in-part of application No. 13/744,807, filed on Jan. 18, 2013.

(60) Provisional application No. 61/720,058, filed on Oct. 30, 2012.

(51) Int. Cl.

| A61K 9/00 | (2006.01) |
|---|---|
| A61K 9/06 | (2006.01) |
| A61K 9/10 | (2006.01) |
| A61K 31/4535 | (2006.01) |
| A61K 45/06 | (2006.01) |
| A61K 31/56 | (2006.01) |
| A61K 31/137 | (2006.01) |
| A61K 31/167 | (2006.01) |
| A61K 31/573 | (2006.01) |
| A61K 47/02 | (2006.01) |
| A61K 9/107 | (2006.01) |
| A61K 9/127 | (2006.01) |
| A61K 9/20 | (2006.01) |

(52) U.S. Cl.
CPC .......... *A61K 9/0014* (2013.01); *A61K 9/0053* (2013.01); *A61K 9/06* (2013.01); *A61K 9/10* (2013.01); *A61K 9/107* (2013.01); *A61K 9/127* (2013.01); *A61K 9/2054* (2013.01); *A61K 31/137* (2013.01); *A61K 31/167* (2013.01); *A61K 31/4535* (2013.01); *A61K 31/56* (2013.01); *A61K 31/573* (2013.01); *A61K 45/06* (2013.01); *A61K 47/02* (2013.01)

(58) Field of Classification Search
None
See application file for complete search history.

(56) References Cited

U.S. PATENT DOCUMENTS

| 3,682,930 | A | 8/1972 | Bourquin et al. |
|---|---|---|---|
| 4,659,716 | A | 4/1987 | Villani et al. |
| 5,595,997 | A | 1/1997 | Aberg et al. |
| 6,207,683 | B1 | 3/2001 | Aberg et al. |
| 6,207,684 | B1 | 3/2001 | Aberg |
| 7,226,934 | B1 | 6/2007 | Aberg et al. |
| 7,557,128 | B2 | 7/2009 | Aberg et al. |
| 8,557,846 | B1 | 10/2013 | Aberg et al. |
| 2008/0287498 | A1 | 11/2008 | Aberg et al. |
| 2010/0105734 | A1 | 4/2010 | Aberg et al. |
| 2010/0130550 | A1 | 5/2010 | Aberg et al. |
| 2010/0249202 | A1 | 9/2010 | Koga et al. |
| 2015/0272941 | A1 | 10/2015 | Aberg et al. |

FOREIGN PATENT DOCUMENTS

| WO | 0119367 A1 | 3/2001 |
|---|---|---|
| WO | 2008153761 A1 | 12/2008 |
| WO | 2009142772 A2 | 11/2009 |
| WO | 2014066212 A1 | 5/2014 |

OTHER PUBLICATIONS

RU 2 226 115 C2 Dec. 20, 2005 (Dec. 20, 2005), 20 pages, with English Abstract.
Baumer; "Sphingosine-1-phosphate and Histamine H4 Receptors as New Therapeutic Targets for Allergic SKin Diseases"; pp. 38-40; from Keynote Lectures; J. Vet. Pharmacol. Therap.; 32(Suppl. 1), pp. 11-46; (2009).
Cowden, et al.; "The Histamine H4 Receptor Mediates Inflammation and Pruritus in Th2-Dependent Dermal Inflammation"; Journal of Investigative Dermatology; 130; pp. 1023-1033; (2010).
Guidance for Industry; "Estimating the Maximum Safe Starting Dose in Initial Clinical Trials for Therapeutics in Adult Healthy Volunteers"; U.S. Department of Health and Human Services Food and Drug Administration Center for Drug Evaluation and Research; 26 pages, Jul. 2005 Pharmacology and Toxicology.
Hiller et al.; "The ACVD Task Force on Canine Atopic Dermatitis (I): Incidence and Prevalence"; Veterinary Immunology and Immunopathology; 81; pp. 147-151; (2001).
International Search Report and Written Opinion; International Application No. PCT/US13/67177; International Filing Date Oct. 29, 2013; Date of Mailing Aug. 12, 2014; 13 pages.
Kennedy, G.R.; "Metabolism and Pharmacokinetics of Ketotifen in Children"; Research and Clinical Forums; 4; pp. 17-20; (1982).
Ketotifen (Systemic); Professional Drug Information, Drugs.com, updated Mar. 6, 2008, Mar. 17, 2008 and Mar. 12, 2008;, printed Jul. 13, 2013; 11 pages.
Lane, D.J.; "A Steroid Sparing Effect of Ketotifen in Steroid-Dependent Asthmatics"; Clinical Allergy; 10; pp. 519-525; (1980).
Le Bigot et al.; "Metabolism of Ketotifen by Human Liver Microsomes_in Vitro Characterization of a Tertiary Amine Glucuronidation"; Drug Metabolism and Disposition; 11(6); pp. 585-589; (1983).

(Continued)

Primary Examiner — Kortney L Klinkel
Assistant Examiner — Tori M Strong
(74) Attorney, Agent, or Firm — Cantor Colburn LLP

(57) ABSTRACT

The methods disclosed herein relate to the treatment of dermal infectious disorders, in human patients, by administering a therapeutically effective amount of RS-norketotifen.

9 Claims, No Drawings

(56) References Cited

OTHER PUBLICATIONS

Maclay et al.; "Postmarketing Surveillance: Practical Experience With Ketotifen"; British Medical Journal; 288; pp. 911-914 (1984).

Murota et al.; "Impact of Sedative and Non-Sedative Antihistamines on the Impaired Productivity and Quality of Life in Patients with Pruritic Skin Diseases"; Allergology International; 59; pp. 345-354; (2010).

Neilly et al.; "Pruritus in Diabetes Mellitus: Investigation of Prevalence and Correlation With Diabetes Control"; Diabetes Care; 9(3); pp. 273-275; (1986).

Nelson, Harold S.; "Beta-Adrenergic Bronchodilators"; Drug Therapy; 33(8); pp. 499-506; (1995).

Nolte et al.; "Inhibition of Basophil Histamine Release by Methotrexate"; Abstract; Agents Actions; 23(3-4); pp. 173-176; (1988).

Polivka et al.; "4H-Benzol[4,5]Cyclohepta[1,2-b]Thiophenes and 9,10-Dihydro Derivatives—Sulfonium Analogues of Pizotifen and Ketotifen; Chirality of Ketotifen; Synthesis of the 2-Bromo Derivative of Ketotifen"; Collect. Czech. Chem. Commun.; 54; 27 pages; 1989.

Prowse, Keith; "Ketotifen in Adult Asthma"; Best Med. J.; 280:646; (1980).

Robbach et al.; "Histamine H4 Receptor Antagonism Reduced Hapten-Induced Scratching Behaviour but not Inflammation"; Experimental Dermatology; 18; pp. 57-63; (2009).

Roquet et al.; "Effects of Loratadine on Anti-IgE-Induced Inflammation, Histamine Release, and Leukocyte Recruitment in Skin of Atopics"; Allergy; 50(5); pp. 414-420; Abstract Only; (1995).

Ruben, Dawn; Diphenhydramine (Benadryl(R)); www.petplace.com/drug-library/diphenhydramine-benadryl/page1.aspx; 2 pages; printed Oct. 16, 2012.

Thomas, Randall C.; "Proceeding of the North American Veterinary Conference, Canine Atopic Dermatitis: Old and New Therapies"; pp. 285-288; (2005).

Tonelli et al.; "A Bio-assay for the Concomitant Assessment of the Antiphlogistic and Thymolytic Activities of Topically Applied Corticoids"; Endocrinology; 77; pp. 625-634; (1964).

U.S. Appl. No. 13/739,090, filed Jan. 11, 2013 NonFinal Office Action Mailed May 3, 2013.

U.S. Appl. No. 13/739,090, filed Jan. 11, 2013; A.K. Gunnar Abert; Medicinal Treatment of Dermal Diseases in Dogs.

U.S. Appl. No. 13/744,807, filed Jan. 18, 2013; Final Office Action, Mailed Aug. 2, 2013; 23 pages.

U.S. Appl. No. 13/744,807, filed Jan. 18, 2013; A.K. Gunnar Abert and Vincent B. Ciofalo; Medicinal Treatment of Atopic Inflammatory Diseases.

U.S. Appl. No. 10/069,663, filed Nov. 29, 2006; 1.132 Declaration of A.K. Gunnar Aberg, filed Dec. 14, 2006; 3 pages.

U.S. Appl. No. 13/744,807, filed Jan. 18, 2013; NonFinal Office Action; Mailed Jun. 7, 2013; 43 pages.

Varsano et al; "Multicenter Study with Ketotifen (Zaditen) Oral Drop Solution in the Treatment of Wheezy Children Aged 6 Months to 3 Years"; Pediatr Allergy Immunol; 4(1); pp. 45-50; (1993) Abstracty Only.

Wauquier et al.; "Further Studies on the Distinctive Sleep-Wakefulness Profiles of Antihistamines (Astemizole, Ketotifen, Terfenadine) in Dogs"; Drug Development Research; 4; pp. 617-625; (1984).

Zaditen; Novartis, Pharmaceutical Information, Product monograph, printed Jul. 16, 2013; 3 pages.

MEDICINAL TREATMENT OF DERMAL INFECTIOUS DISORDERS WITH NORKETOTIFEN

CROSS-REFERENCE TO RELATED APPLICATIONS

This application is a continuation of U.S. application Ser. No. 14/437,534 filed on Apr. 22, 2015, which is a §371 of PCT/US2013/067177 filed on Oct. 29, 2013, which claims priority and is a continuation in part of U.S. application Ser. No. 13/744,807, filed on Jan. 18, 2013, which claims priority from U.S. Provisional Application Ser. No. 61/720,058, filed on Oct. 30, 2012, under the provisions of 35 U.S.C. §119 and the International Convention for the Protection of Intellectual Property, the disclosure of which is hereby incorporated by reference.

TECHNICAL FIELD

The embodiments disclosed herein relate to methods for the treatment of chronic inflammatory, infectious, and allergic pulmonary diseases in humans, while avoiding side effects that are commonly associated with anti-inflammatory antihistamines.

BACKGROUND

Ketotifen (Zaditen®, Zaditor®, Sandoz, Novartis) is a Generation-1 antihistamine that is mainly used for the treatment of allergic rhinitis. Ketotifen may be the most sedating of all marketed antihistamines, and the unusually severe sedative side effects of ketotifen have limited the therapeutic usefulness of the drug. In the USA, ketotifen is only used as eye drops (Zaditor®, Novartis) to alleviate the symptoms of allergic conjunctivitis in humans, and does not cause sedation due to the extremely low systemic concentrations of the drug after local administration to the eyes.

Other anti-inflammatory H-1 antihistamines are, for example, azatadine (Zadine®, Schering-Plough), chlorpheniramine (Qdall®, Atley Pharmaceuticals), mepyramine (Pyrilamine®, Rhone-Poulenc, Tocris) and promethazine (Phenergan®, Baxter). All have antihistaminic (H-1) activity and all cause sedation and drowsiness.

Norketotifen (synonymously called RS-norketotifen), a hepatic metabolite of ketotifen, is an achiral molecule, but has two atropisomers, S-norketotifen and R-norketotifen, as has previously been described in U.S. Pat. Nos. 7,226,934 and 7,557,128. As explained in U.S. Pat. Nos. 7,226,934 and 7,557,128, norketotifen also had a significant sedation effect when studied in the art-accepted, and carefully validated mouse model of sedation, and further, the sedative effects were attributed to the R-isomer. It was thus proposed that only the S-isomer could be administered without sedative side effects.

Atopic dermatitis (AD) is a chronic allergic skin disease that occurs in 10 to 20 percent of children and 1 to 3 percent of adults. Of all patients suffering from AD, 40 to 60 percent also have respiratory allergies. Psoriasis is a chronic autoimmune dermal disease, caused by overproduction of new skin cells. Approximately 2.2 percent of the U.S. population suffers from psoriasis. Like patients with AD, psoriasis patients suffer from pruritus. Compromised skin barrier function has a role both in AD and psoriasis.

Many fungi have been described as normally living on the skin of various mammal species, including humans. Malassezia species form a family of lipolytic fungi that currently is believed to include 14 species. Overgrowth of Malassezia species causes toxic and/or immunological reactions and contributes to both AD and psoriasis, and also contributes to various other dermal diseases and conditions, such as for example, adult seborrheic dermatitis, dandruff, Malassezia folliculitis, tinea versicolor and rosacea. These fungal disorders are typically treated with medication for the underlying condition in combination with an antifungal mediation that can be administered orally or topically (dermally) to the skin.

Dermal bacterial infections are common in patients suffering from many dermal diseases, such as for example atopic dermatitis and psoriasis. These infections are often causative, as allergic reactions with inflammation and pruritus may be triggered by for example Staphylococcus aureus. As pointed out by Breuer et al., Allergy 2001, 56: 1034-1041, (2001), the skin of about 80 to 100 percent of patients with atopic dermatitis is colonized with Staphylococcus aureus, while Staphylococcus aureus can be found on the skin of only 5 to 30 percent of normal individuals. Breuer et al. (2001) and others have noted that the density of Staphylococcus aureus is increased according to the disease severity and that Staphylococcus aureus is causative for atopic dermatitis, since this bacterium promotes inflammation due to the action of superantigens. It was found by Brockow et al., Dermatology 1999, 199: 231-236 (1991) that topical antibacterial therapy in combination with an anti-inflammatory steroid not only reduced Staphylococcus aureus, but also reduced the severity of atopic dermatitis.

What is needed are methods of treating inflammatory dermal disorders without causing sedation or the much feared side effects of corticosteroids and immunosuppressant drugs. Also needed are improved topical treatments for combined inflammatory and infectious dermal disorders. Both topical and oral anti-pruritic medications are also needed.

SUMMARY

In one aspect, a method of treating chronic inflammatory dermal disorders in a human patient in need of such treatment comprises orally administering to the human patient in need thereof a therapeutically effective amount of RS-norketotifen or a pharmaceutically acceptable salt thereof is 0.5 to 20 mg dosed once or more daily, and wherein the therapeutically effective amount does not produce sedative side effects upon administration to the human patient.

In another aspect, a method of treating a chronic atopic inflammatory dermal disorder in a human patient comprises determining whether said patient is susceptible to adverse sedative effects of compounds with antihistaminic activity, and if said determination is positive, administering to said patient in need thereof an oral formulation comprising a therapeutically effective amount of RS-norketotifen or a pharmaceutically acceptable salt of RS-norketotifen that is 0.5 to 20 mg, dosed orally once or more daily.

A method of treating skin infections in a human patient suffering from a skin infection comprises topically administering a topical formulation to an infected skin lesion and areas adjacent to the skin lesion on the human patient, wherein the topical formulation comprises a therapeutically effective amount of RS-norketotifen or a pharmaceutically acceptable salt thereof and a pharmaceutically acceptable excipient.

DETAILED DESCRIPTION

The methods disclosed herein relate to the treatment of pruritic, inflammatory, and/or infectious dermal disorders, such as for example eczema, atopic dermatitis, urticaria and psoriasis, in human patients, by administering the anti-inflammatory, anti-allergic, and anti-microbial compound, norketotifen and pharmaceutically acceptable salts thereof. Prior to the present disclosure, the therapeutically important efficacy of norketotifen and the two isomers thereof had not been reported. In certain aspects, administration is oral administration, topical administration, or a combination thereof.

It had previously been found and described that both ketotifen and norketotifen express sedative activity, and were therefore not considered to be useful as oral medications for the treatment of chronic diseases, such as for example, atopic dermatitis. Sedation was determined using a mouse model that has previously been used successfully in the development of non-sedating antihistamines, such as loratadine (Claritin®, Schering) and desloratadine (Clarinex®, Schering). It was therefore believed that the mouse model had relevance for evaluating the clinical use of the current benzocycloheptathiophene compound that has potent antihistaminic activities. The mouse model clearly demonstrated the sedative effects of racemic norketotifen and R-norketotifen.

It has now surprisingly been found that racemic norketotifen is completely free from sedative effects when orally administered to humans, even after repeated administration of high doses of the compound.

It has further been unexpectedly discovered that norketotifen and its isomers have antimicrobial activity and can be used to inhibit the growth of microorganisms such as fungi and bacteria including *Malassezia* sp, *Candida albicans*, and *Staphylococcus aureus*. Thus, in one aspect, disclosed herein is a method of treating skin infections in a human patient comprising administering to the skin (e.g., an infected skin lesion and adjacent areas) of the human patient a topical formulation comprising a therapeutically effective amount of norketotifen or a salt or isomer thereof and a pharmaceutically acceptable excipient. Skin infections can also be treated by oral administration of norketotifen.

In one aspect, the active compound is racemic norketotifen, herein often called RS-norketotifen or just norketotifen. Norketotifen is an achiral molecule, but has two isomers, S-norketotifen and R-norketotifen, as has previously been described in U.S. Pat. Nos. 7,226,934 and 7,557,128. Norketotifen is particularly useful for both oral and topical administration.

Chemically, norketotifen is (RS)-4-(piperidylidene)-9,10-dihydro-4H-benzo-(4,5)-cyclohepta-(1,2-b) thiophene-10-one. The prefix (RS) can optionally be excluded when referring to racemic norketotifen.

Norketotifen is a metabolite of ketotifen (4-(1-methyl-4-piperidyline)-4H-benzo(4,5)-cyclohepta-(1,2-b) thiophene-10-one). Ketotifen may be the most sedating of all marketed antihistamines and the unusually severe sedative side effects of ketotifen has limited the therapeutic usefulness of the drug to 1 mg, bid to when administered orally in the treatment of atopic dermatitis human.

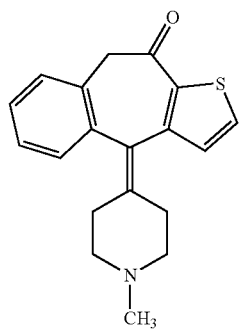

KETOTIFEN

The metabolite norketotifen is formed by demethylation of ketotifen in the liver of humans and it has been calculated that up to 0.5 mg norketotifen is formed in the liver of human patients after an oral dose of one milligram ketotifen:

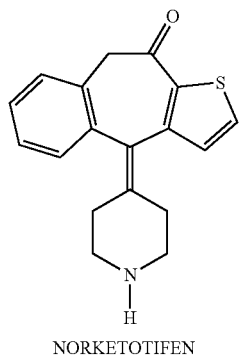 [SMILES: O=C1Cc2ccccc2C(=C2CCNCC2)c2ccsc21]

NORKETOTIFEN

Norketotifen can be made from methods known in the art, as described in U.S. Pat. No. 3,682,930, the disclosure of which is hereby incorporated by reference for its teaching of the synthesis of norketotifen.

Except for U.S. Pat. Nos. 7,226,934 and 7,557,128, no publications are known that describe the pharmacodynamic activities of RS-norketotifen. U.S. Pat. No. 6,207,684 and Publications 2010/0105734 and 2010/0130550 describe the effects of RS-norketotifen when used as eye drops for ocular indications, such as allergic conjunctivitis and xerophthalmia in humans.

Certain embodiments disclosed herein provide for the oral administration of the racemic form of norketotifen or pharmaceutically acceptable acid addition salts of the compound to human patients in need thereof. Norketotifen is ideally suited for the treatment of atopic dermatitis (AD), since this compound, has potent anti-inflammatory and antipruritic effects, and has now, surprisingly, been found to be completely free from sedative side effects and to have antimicrobial effects of significant importance. In a specific embodiment, the norketotifen is racemic norketotifen.

In one embodiment, norketotifen is administered to the patient orally. In another embodiment, the administration is topical (dermal or rectal) administration to the skin of the human patient and in still another embodiment, norketotifen is administered to the patient by inhalation. In one embodiment, administration is oral administration. In another embodiment, administration is by inhalation Atopic inflammatory disorders in humans can be caused by various allergens, such as for example airborne or food allergens, fleas, bacteria, fungi or contact allergens.

Atopic inflammatory disorders include dermal disorders such as for example eczema, atopic dermatitis, urticaria and psoriasis. Pulmonary disorders include for example asthma, COPD, cough, bronchial hyperactivity, and bronchitis, and gastrointestinal disorders including gastric irritation, gastric allergic disorders, and gastric inflammatory disorders. Examples of gastric inflammatory disorders are for example various eosinophilic gastrointestinal disorders, such as for example eosinophilic esophagitis, eosinophilic gastroenteritis and other forms of gastrointestinal eosinophilia.

In one embodiment, a method for reducing sedative side effects in the treatment of pruritic and/or inflammatory dermal disorders in a human patient in need of such treatment comprises orally administering to the patient in need thereof a therapeutically effective amount of norketotifen or a pharmaceutically acceptable salt thereof that does not produce sedative side effects upon administration to the human patient. In one embodiment, treatment is chronic, subchronic, or acute, specifically chronic. As used herein chronic administration is three or more consecutive days of administration. Acute refers to a single administration. Subchronic refers to less than 3 consecutive days of administration. In a specific embodiment, the norketotifen is racemic norketotifen.

In another aspect, disclosed herein is a method of treating a human patient in need of treatment for a skin infection comprising administering to the skin (e.g., to an infected skin lesion and the infected adjacent non-lesion skin on the patient) a topical formulation comprising a therapeutically effective amount of norketotifen or a salt or isomer thereof together with one or more pharmaceutically acceptable excipient(s). Oral administration can be used in addition to or as an alternative to topical administration. Both bacteria and fungi can be found in skin lesions and in areas of the adjacent to the lesions on humans suffering from atopic dermatitis. *Staphylococcus aureus* bacterial infections are common in human patients with AD and very prevalent in lesions and in normal skin adjacent to the lesions. *S. aureus* is believed to be causative for some of the manifestations of atopic dermatitis since a toxin that is produced by the bacteria (*staphylococcus* enterotoxin B) has been found to induce both induration and erythema of the skin of healthy human volunteers and volunteers with atopic dermatitis.

*Candida albicans* dermal fungal infections are common among human patients with atopic dermatitis and clinical studies have linked the presence of anti-*Candida albicans* antibodies in the blood with the clinical condition of atopic dermatitis.

*Malassezia* sp dermal fungus and in particular *Malassezia globosa* is probably the most common microorganism in infected human skin lesions, and is also known to cause exacerbation of the disease and to cause intense pruritus. *M. globulosa, M. sympodialis* and *M. furfur* cause Tinea versicolor, which is a chronic superficial fungal infection in humans with a prevalence of 30-40 percent in tropical areas. *M. furfur* and possibly other *Malassezia* species, can induce the overproduction of molecules (such as TGF-beta-1) involved in cell migration and hyperproliferation, thereby favoring the exacerbation of psoriasis.

Bacterial skin infections can result from opportunistic microbes causing infections in patients with an underlying immune disorder, allergies, hormonal disease, liver disease and kidney disease, for example. Inflammation and scratching break down dermal barriers leading to the worsening of dermal infections.

Infected skin lesions can be readily identified by visual inspection and/or skin cytology of the lesions. Cells from the lesion are stained and then examined under a microscope. Both fungi and bacteria can be identified in this manner by different stains as well as the shape of the cells. In addition, the underlying causative microorganism can be identified by cell culture techniques.

Norketotifen is particularly useful in the treatment of human patients who are susceptible to sedation upon administration of drugs with antihistaminic activity. Sedation is a common side effect of antihistamines such as diphenhydramine, which is a sedating Generation-1 antihistamine without anti-inflammatory activity used mainly for the treatment of allergic rhinitis. Ketotifen is also known to cause sedation. For some patients, the sedative side effects can outweigh the benefits of such medication, particularly in the treatment of chronic, non-life-threatening conditions such as dermal disorders, such as for example atopic dermatitis, and pulmonary disorders, such as for example asthma. While allergic rhinitis is a highly seasonal condition, dermal and pulmonary disorders most often require year-round treatment over multiple years. Sedation over long periods of time is not acceptable. Further, while non-sedating antihistamines are available, these drugs do not have the anti-inflammatory activity needed for the treatment of inflammatory disorders, such as for example atopic dermatitis and asthma. Because of the previous belief that norketotifen has similar sedative side effects as ketotifen, one would not have used this compound to treat chronic allergic/inflammatory disorders in patients susceptible to sedative side effects.

Those skilled in the art know how to determine if a patient is susceptible to sedation from sedative (Generation-1) compounds. For example, the oral administration of a single daily clinical dose of ketotifen will cause sedation (drowsiness) in individuals susceptible to sedative side effects, but the dose of ketotifen will not cause sedation in individuals who are not susceptible to sedative side effects of Generation-1 antihistaminic drugs. Likewise, a high clinical dose of diphenhydramine can be used to differentiate between patients who are susceptible to sedation and those who are not susceptible to the sedative side effects of Generation-1 antihistaminic drugs.

In one embodiment, the doctor may determine if a patient suffering from an atopic inflammatory disorder is susceptible to sedative side effects, for example, by using one of the methods described above. If the patient is susceptible to sedative side effects, the patient can safely be administered norketotifen for treatment of chronic atopic inflammatory disorders.

The embodiments disclosed herein also provide pharmaceutical compositions, which comprise the compound of the invention, formulated together with one or more pharmaceutically acceptable carriers. The pharmaceutical compositions may be formulated for oral administration, sublingual administration, parenteral administration, dermal administration (application), transdermal administration, rectal administration, buccal administration, for topical administration, or pulmonary administration such as administration by inhalation, or insufflation of dry powder or aerosol.

Pharmaceutical compositions for oral administration of solid dosage forms include capsules and tablets. In solid dosage forms, the active compound may be mixed with one or more pharmaceutically acceptable excipients or carriers (such as for example sodium citrate, dicalcium phosphate), fillers or extenders (such as for example starch, lactose, sucrose, glucose, mannitol, silicic acid), binders (such as for example alginates, carboxymethylcellulose, gelatin, polyvinylpyrrolidone, sucrose, acacia), humectants (such as for example glycerol), solution retarding agents (such as for example paraffin), disintegrating agents (such as for example agar-agar, calcium carbonate, starch, alginic acid, silicates, sodium carbonate), absorption accelerators (such as for example quaternary ammonium compounds), wetting agents (such as for example cetyl alcohol, glycerol monostearate), absorbents (such as for example kaolin, bentonite clay), lubricating agents (such as for example talc, calcium stearate, magnesium stearate, polyethylene glycols, sodium lauryl sulfate), and/or other excipients, such as for example buffering agents. Solid forms of capsules, granules, pills, and tablets can have coatings and/or shells (such as for example enteric coatings) known in the art. The compositions may also be designed to release the active ingredient(s) in a certain part of the gastrointestinal tract or in a controlled release, slow-release or in a delayed-release manner. The active compound(s) can also be micro-encapsulated with one or more of the above-mentioned excipients or other suitable excipients.

Liquid dosage forms for oral administration include pharmaceutically acceptable emulsions, solutions, suspensions, syrups and elixirs. The liquid dosage form may also contain commonly known diluents (such as for example water, other solvents, solubilizing agents), emulsifiers (such as for example ethanol, isopropyl alcohol, ethyl carbonate, ethyl acetate, benzyl alcohol, benzyl benzoate, propylene glycol, butylene glycol, dimethyl formamide, oils, oleic acid, glycerol, polyethylene glycols, sorbitan fatty esters, and mixtures thereof.)

The oral compositions may also include other excipients as known to those skilled in the art.

Pharmaceutical compositions for parenteral injections include pharmaceutically acceptable sterile solutions, dispersions, suspensions, emulsions and sterile powders for reconstitution into sterile injectable solutions or dispersions prior to use. Various carriers, diluents, solvents and vehicles may be used.

Parenteral compositions may also contain excipients such as for example preservatives, wetting agents, emulsifying agents, dispersing agents, isotonic agents, and/or absorption-delaying agents. Absorption-prolonging or absorption-slowing effects may be achieved by injecting a crystalline or amorphous suspension with low water solubility. Delayed absorption may also be obtained by dissolving or suspending the drug in an oil vehicle or by using injectable depot forms (ex. microencapsulated matrices of the drug in biodegradable polymers, such as polylactide-polyglycolide, polyorthoesters, polyanhydrides) or by using various types of liposomes or microemulsions to hold the drug. Formulations for injection can be sterilized by various methods.

Pulmonary administration, such as by inhalation or insufflation, may be accomplished, for example, using an aerolizer, a nebulizer, a dry powder inhaler, a metered dose inhaler, and the like.

Pharmaceutical compositions for topical application of norketotifen include, for example, pharmaceutically acceptable solutions, emulsions, creams and ointments, preferably containing 0.1 percent to 10 of norketotifen or a pharmaceutically acceptable salt thereof, which may be applied one or more times daily. The topical formulations will also contain one or more pharmaceutically acceptable excipients.

A large number of excipients have now been tested for compatibility with norketotifen, and excipients have been identified that are compatible with norketotifen. Examples of compatible excipients, are antioxidants, such as sulfites or ascorbates, at concentrations of about 0.05 percent to about 3 percent, specifically about 0.1 percent to about 0.25 percent by weight; buffering agents, such as for, example, phosphates, borates, citrates and acetates, at concentrations of about 0.01 percent to about 4 percent by weight; chelating agents, such as, for example, edetate or chitosan polysaccharides, at concentrations of about 0.01 percent to about 10 percent, specifically about 0.01 percent to about 2.0 percent by weight; emollients, such as, for example, glycerin or propylene glycol, at concentrations of about 0.1 percent to about 10 percent, specifically about 0.1 percent to about 2.0 percent by weight; gelling agents, such as, for example, alginates or gelling polymers, at concentrations of about 0.05 percent to about 10 percent, specifically about 0.1 percent to about 2.5 percent by weight; in situ gelling agents, such as alginate/HPMC (hydroxypropyl methylcellulose) or polyacrylic acid (Carbopol)/HPMC, at concentrations of about 0.5 percent to about 10 percent, specifically about 0.1 percent to about 2.5 percent by weight; humectants, such as, for example, polyethylene glycol or propylene glycol, at concentrations of about 0.05 percent to about 10 percent by weight; stabilizers, such as methylcellulose or chitosan, at concentrations of about 0.05 percent to about 4 percent, specifically about 0.05 percent to about 2.0 percent by weight; combined stabilizer/solubilizers, such as for example $\alpha$-, $\beta$- or $\gamma$-cyclodextrin, at concentrations of about 0.1 percent to about 20 percent by weight; surfactants, such as, for example glyceryl stearate or polyethoxylated castor oil, at concentrations of about 0.05 percent to about 4.0 percent, specifically about 0.1 percent to about 2.0 percent by weight; and viscosity-adjusting agents, such as, for example, methylcellulose or propylene glycol alginate, at concentrations of about 0.1 percent to about 10 percent, specifically about 2.0 percent to about 5.0 percent by weight.

Numerous compositions using said excipients have been prepared and tested using an HPLC method for the determination of concentrations of norketotifen that has been developed for this purpose.

The actual dosage levels of active ingredients in the pharmaceutical compositions disclosed herein may be varied so as to obtain the desired therapeutic effect. Thus the amount of drug used varies and will depend on factors such as the administration form, the severity of the disease, the frequency of dosing, and other circumstances (such as general health, age, etc.) known to the patient, the caretaker of the patient and/or the caring physician.

The therapeutically effective oral doses of norketotifen useful for treating human patients with atopic dermatitis (AD) will be determined by the caring physician and are generally 0.5 mg to 20 mg (calculated as free base), dosed orally as the free base or as a salt, such as for example the hydrochloride or mesylate salts or the hydrogen fumarate salt, once, twice or more times daily. In one embodiment, the treatment is once daily dosing. The therapeutically effective dose may be administered less than once daily, such as for example two to six times weekly, as determined by the patient, the caretaker of the patient and/or the caring physician. Typically, after therapeutic efficacy has been established, the dosing of norketotifen may be decreased from daily dosing to dosing two to six times weekly.

The actual dosage levels of norketotifen in the topical compositions disclosed herein may be from 1 percent to 10 percent by weight, but may be varied so as to obtain the desired therapeutic effect.

In general, the therapeutically active pulmonary doses of norketotifen, useful for treating patients with the previously defined pulmonary diseases, are 0.5 mg to 20 mg administered with an aerolizer, a nebulizer, a dry powder inhaler, a metered dose inhaler, and the like, once or more times daily.

The embodiments disclosed herein provide methods for treatment of immunologic, inflammatory and skin disorders in human patients, while avoiding the sedating side effects of ketotifen. The embodiments also provide treatment of dermal microbial disorders in human patients. These methods comprise administering to the human patient in need of such treatment, effective amounts of norketotifen free base or a pharmaceutically acceptable salt thereof, at a dosing frequency to be determined by the individual human patient, the caretaker of the patient and/or the caring physician. In one embodiment, dosing frequency is once daily, while the topical dosing frequency is one or multiple times daily.

In addition to the use of norketotifen as single-drug medication in human patients, embodiments disclosed herein also provide methods for co-administration of norketotifen with at least one drug of the following classes: adrenergic beta-agonists, insecticidal agents, antibacterial agents, antiviral agents, vitamin D or vitamin D analogs, corticosteroids, cyclooxygenase inhibitors, leukotriene antagonists, lipoxygenase inhibitors, inhibitors of one or more cytokines, such as for example kinase inhibitors and immunomodulators, such as for example cyclosporine. The co-administration may be temporary or may be chronically used in the patient. The co-administered drug can be administered to the patient separately or can be co-formulated with norketotifen for oral, parenteral, pulmonary or dermal administration. Thus, as an example, norketotifen can be administered orally and/or topically and the co-administered drug may also be administered orally or topically. Furthermore, norketotifen and the co-administered drug may not be administered simultaneously. Thus, as an example, norketotifen may be administered orally once daily, while a co-administered corticosteroid may be administered orally or topically, one or more times daily.

Of specific importance is co-administration of norketotifen with an anti-inflammatory corticosteroid, since onset time of the therapeutic activity of norketotifen in dogs suffering from atopic dermatitis may be shortened by said co-administration. For this purpose, norketotifen can be combined with a corticosteroid, for example for the first one to four weeks of therapy. The full-dose dose of the corticosteroid depends on the potency of said corticosteroid. High-potency or mid-potency corticosteroids are preferred. As an example, if the mid-potency corticosteroid is used in combination with norketotifen, the regular dose of said corticosteroid may be 0.1 to 5.0 mg (dosed once or multiple times daily) and can be combined with a regular oral dose of norketotifen, which may be from 0.5 mg to 20 mg (dosed once or multiple times daily and calculated as free base) to the selected patient. The combination treatment of norketotifen and a corticosteroid like prednisone or prednisolone can be administered to patients suffering from atopic dermatitis and other dermal diseases. The combination of norketotifen and a corticosteroid can be administered in double dose for the first one to seven days of therapy. Following the initial treatment of the human patient with a combination of norketotifen and a corticosteroid, the continued treatment will consist of norketotifen monotherapy, as described above.

In one embodiment, norketotifen is initially orally or topically co-administered for one to four weeks of therapy with a corticosteroid in a therapeutically active dose, thereafter followed by monotherapy, wherein norketotifen or a pharmaceutically acceptable salt thereof, when orally administered, is administered in an amount of 0.5 mg to 20 mg, dosed once or multiple times daily and calculated as free base.

Those skilled in the art of pharmacology will realize that corticosteroid-sparing doses will be obtained by co-administration of norketotifen at normal, oral daily doses of between 0.5 mg and 20 mg dosed once or multiple times daily and calculated as free base with doses of corticosteroids that are lower than said doses when the corticosteroids are administered as monotherapy. Thus, in patients suffering from atopic dermatitis, it will be possible to reduce the common therapeutic doses of corticosteroids up to 50 percent or more by co-administration of norketotifen at doses ranging from 0.5 mg to 20 mg dosed once or multiple times daily and calculated as free base. A regular dose of prednisone to patients suffering from atopic dermatitis depends on the size and age of the patient and the severity of the disease and may range from 0.5 mg to 20 mg once or multiple times daily, or the dose may be higher in selected patients. During co-administration with norketotifen the doses of prednisone in the patient may be decreased to between 0.2 mg and 10 mg, or the doses of the steroid may be reduced further in selected patients, which reductions are herein considered to be "half the regular dose" of said steroid. As usual, the actual doses to individual patients may vary due to various factors, such as for example the severity of the medical conditions, tolerance to acute drug side effects, age and weight of the patient. Thus the doses of the corticosteroid to individual patients may be higher or lower than described herein.

When used for the treatment of dermal disorders other than atopic dermatitis in human patients, co-administration of norketotifen and a corticosteroid, such as for example prednisone, will result in a corticosteroid-sparing treatment. The same doses of norketotifen and the corticosteroid as described herein for corticosteroid-sparing treatment of atopic dermatitis, can be used. As always, the dose to an individual patient will have to be modified according to the weight and age of the patient, the severity of the disease and other circumstances known to the patient, caretaker of the patient and/or the caring physician.

Similarly, it will be possible to reduce the doses of an immunosuppressant drug, such as for example cyclosporine with co-administration of norketotifen. Thus, in patients suffering from atopic dermatitis, it will be possible to reduce common therapeutic doses of an immunosuppressant drug by 50 percent or more by co-administration of norketotifen at normal oral doses of norketotifen, which are ranging from 0.5 mg to 20 mg, once or multiple times daily, thereby reducing the potentially very serious side effect of the immunosuppressant drug. As an example during co-administration with a normal dose of norketotifen, the initial dose of the immunosuppressant drug cyclosporine may be decreased in a selected patient from about 2 mg/kilogram bodyweight/day to about 1 mg/kilogram bodyweight/day, which is an example of what herein is called "half the regular dose". The dose of the immunosuppressant drug can be further reduced by dosing the drug every other day, or even more seldom. Examples of immunosuppressant drugs are cyclosporine (Atopica®, Novartis), pimecrolimus (Elidel®, Novartis, Meda), tacrolimus (Protopic®, Astellas Pharma) and oclacitinib (Apoquel®, Zoetis). Some immunosuppressant drugs can also be called immunomodulating drugs or calcineurin inhibitors.

When used for treatment of other dermal disorders than atopic dermatitis in human patients, co-administration of norketotifen and an immunomodulating drug, such as for example cyclosporine, will use the same dose-ranges as described herein for the treatment of atopic dermatitis. As always, the dose to an individual dog will have to be modified according to the drug used, the weight of the patient, the severity of the disease and other circumstances known to the patient, the caretaker of the patient and/or the caring physician.

In one aspect, topical drug administration of norketotifen is combined with oral administration of norketotifen. For example, a child suffering from atopic dermatitis may have patches of skin that become infected by the fungus *Malassezia*, due for example, to excessive scratching of the skin. By combining systemic (oral syrup) administration and local (topical cream) administration, both the skin infection and the underlying dermatitis can be treated simultaneously. Advantageously, neither the oral nor the dermal administration of norketotifen will be expected to produce sedation of the patient.

When used for pulmonary inflammatory indications, such as for example asthma, COPD, chronic bronchitis and bronchial hyperreactivity, norketotifen can be combined with a therapeutically active dose of a bronchodilating adrenergic beta-receptor agonist and one or both of the drugs can be administered by inhalation, nasal, parenteral, topical, transdermal, rectal, sublingual or oral administration. The adrenergic beta-receptor agonist can be selected from the group consisting of albuterol (salbutamol), terbutaline, fenoterol, formoterol, and salmeterol and the optically and therapeutically active isomers of the beta-receptor agonists. Since bronchial inflammation and broncoconstriction are hallmarks of asthma, the co-administrations of the anti-inflammatory drug norketotifen and a bronchodilating adrenergic beta-agonist will be advantageous to patients suffering from asthma and other pulmonary disorders. An additional advantage is the known inhibition of beta-receptor downregulation by certain anti-inflammatory drugs. In one embodiment, the method further comprises co-administering a steroid with norketotifen and an adrenergic beta-agonist.

In one embodiment, norketotifen and an adrenergic beta-receptor agonist are co-administered in a formulation suitable for pulmonary administration.

EXAMPLES

Example 1

Antihistaminic Activity in vitro $H_1$ receptor binding studies were conducted utilizing human recombinant receptors. In the studies shown herein, affinities of the test compounds for histamine $H_1$-receptors were assessed using a binding assay, where [$^3$H] pyrilamine was used as the ligand and the test compounds were used at increasing concentrations. The specific binding of the radioactive ligand to the receptor was defined as the difference between total binding and nonspecific binding, determined in the presence of excess unlabeled ligand. $IC_{50}$ values (the concentration that inhibits 50% of specific binding of the ligand) are determined by non-linear regression analysis of the competition curves. The results are shown in Table 1.

TABLE 1

| Antihistaminic activity in vitro | |
|---|---|
| ANTIHISTAMINE | H-1/IC50 (nM) |
| KETOTIFEN | 2.3 |
| NORKETOTIFEN | 11 |

TABLE 1-continued

| Antihistaminic activity in vitro | |
|---|---|
| ANTIHISTAMINE | H-1/IC50 (nM) |
| LORATADINE (Claritin ®) | 1,500 |
| DESLORATADINE (Clarinex ®) | 16 |
| DIPHENHYDRAMINE (Benadryl ®) | 84 |

Ketotifen is probably the most potent antihistaminic compound ever to be approved as a drug for human use. Norketotifen has less affinity for the histamine H-1 receptors than ketotifen, but is more potent than the three reference compounds. Loratadine is a poorly active prodrug and is metabolized in the liver to desloratadine.

Example 2

Antihistaminic Activity in vivo

Male rats (150-200 g) were fasted overnight and twelve hours after dorsal depilation, the animals were orally pre-treated with the test compound(s). Four dorsal test areas were marked with permanent ink, carefully avoiding the area closest to the spine. Sixty minutes after the dosing with the test compound, two intradermal injections of histamine (50 µL; 1.0 mg/ml of histamine di-HCl) were performed, one on each side on the back of the animal. Two intradermal injections of the vehicle for the histamine solution were also performed. Evans blue dye (20 mg/kg) was injected intravenously one minute prior to the intra-dermal injections of histamine and the histamine vehicle. Twenty minutes were allowed for the wheal response to fully develop, whereupon the animals were euthanized and the dorsal skin with the intradermal wheals were deflected. The blue spotted areas were measured in square millimeters and the duplicate wheal areas were averaged. In vehicle-treated animals, the wheal area, on average, was increased by histamine by 94 and 82 mm² for the vehicles used during the norketotifen and ketotifen experiments, respectively. The inhibition was calculated in percent difference from said baseline values. Results are shown in Table 2. (DPH=diphenhydramine, Benadryl®)

TABLE 2

| Antihistaminic activity in vivo | | | | |
|---|---|---|---|---|
| Test compound Dose (mg/kg) | Histamine (mm²) | Saline (mm²) | Histamine effect (mm²) | Inhibition (%) |
| Vehicle* | 116 ± 5 | 22 ± 1 | 94 | — |
| Vehicle** | 107 ± 4 | 25 ± 1 | 82 | — |
| Ketotifen; 1.0 | 68 ± 6 | 21 ± 2 | 47 | 43 |
| Ketotifen; 10 | 24 ± 2 | 22 ± 3 | 2 | 98 |
| Norketotifen; 1.0 | 114 ± 8 | 22 ± 1 | 92 | 2 |
| Norketotifen; 10 | 39 ± 2 | 22 ± 1 | 17 | 82 |
| Norketotifen; 50 | 10 ± 1 | 12 ± 1 | 0 | 100 |
| DPH; 10 | | | | 31 |

*Vehicle for norketotifen expts
**Vehicle for ketotifen expts

Results: When plotted, ketotifen was found to be 2 to 3 times more potent than norketotifen as an antihistamine in these in vivo studies. Norketotifen was significantly more potent than diphenhydramine.

Example 3

Anti-inflammatory Effects in vitro

In these studies, histamine was the marker compound for inflammatory mediators that are released from mast cells and other pro-inflammatory cells in patients with atopic inflammatory diseases. The inhibition of stimulated histamine release from human leukocytes (buffy coat) by test articles was studied. Leukocytes were obtained from healthy volunteers and histamine release was induced by incubation (20 min/37° C.) with the calcium ionophore A23187 (5 μM) in the presence or absence of a test article. Histamine was analyzed by enzyme-immune assays, using commercially available kits and a microplate reader (MRX, Dynatech). The test articles were evaluated, in duplicate, at five concentrations. The study results are shown in Table 3.

TABLE 3

Inhibition of inflammatory mediator (histamine) release.

| Test article | IC50 (μM) |
|---|---|
| Ketotifen | 91 |
| Norketotifen | 9.2 |

Norketotifen was approximately 10 times more potent than ketotifen as an inhibitor of histamine release from pro-inflammatory cells.

Example 4

Anti-inflammatory Effects in vivo: Oral Administration

In order to investigate the effects of oral administration of the test compounds in dermal inflammation, a croton oil model was used as is known in the art. This test consists of topical application of 20 μl of 1.0% croton oil to each ear of male mice, weighing 28-32 g. The weight of untreated ears of these animals is 30-32 mg. Application of the croton oil results in an inflammatory response. The weight of croton oil-treated ears was determined and the percent increase in ear weight is calculated. Test articles were dosed systemically (ip).

The effects of 10 mg/kg of RS-ketotifen and RS-norketotifen at 90 and 120 minutes after administration of test articles are shown in the following table. All results represent mean ear weights (±S.E.M.) from 10 ears. The results are shown in Table 4.

TABLE 4

Anti-inflammatory effects in vivo; oral administration

| | Average Ear weight (mg) ± SEM | |
|---|---|---|
| Test Article | 90 min | 120 min |
| Control | 48 ± 2 | 51 ± 2 |
| Ketotifen | 37 ± 1 | 42 ± 1 |
| Norketotifen | 34 ± 1 | 40 ± 1 |

Both test compounds demonstrated dermal anti-inflammatory effects. All or part of the anti-inflammatory effect of ketotifen is assumed to be due to norketotifen that is rapidly formed as a metabolite of ketotifen after oral administration of ketotifen to rodents Example 5

Antipruritic Effects in vivo: Oral Administration

Antipruritic effects were tested in vivo in CD-1 female mice aged 10-12 weeks. The hair was clipped over the rostral part of the back at the interscapular level of the mice one day before dosing. Before testing, the mice were placed in individual clear plastic cages for at least one hour for acclimation. After fasting for 1.5 hours, the animals were dosed orally with the test article, dissolved in a vehicle consisting of 1% methylcellulose/water, 10 mL/kg bodyweight. Sixty minutes after oral dosing, an intradermal injection of histamine (300 nmol in 20 μl phosphate buffered saline (PBS), pH 7.4) was administered into the clipped area. Immediately after the histamine injection, the bouts of scratches were counted for 40 minutes. Scratching induced by the histamine vehicle PBS served as control.

Norketotifen was tested in escalating doses. In addition, a supramaximal dose of 100 mg/kg of norketotifen was tested. The reference compounds JNJ7777120, desloratadine and oclacitinib were dosed orally at 20 mg/kg. The vehicle for the reference compound JNJ7777120 was 20% hydroxypropyl-β-cyclodextrin in water. The vehicle for the reference compound desloratadine was the same as the vehicle for norketotifen. The reference compound desloratadine is a selective histamine H-1 inhibitor, oclacitinib is a Jason I/II kinase inhibitor and JNJ7777120 is a selective histamine H-4 inhibitor.

The test results are shown in Table 5. The numbers of pruritic bouts for Norketotifen, DES and OCLA are expressed in percent of the same Vehicle (100% corresponds to 92 pruritic bouts). Norketotifen inhibited histamine-induced pruritus in a dose-dependent manner and a supramaximal dose (100 mg/kg) demonstrated complete inhibition. A test of the vehicle for JNJ demonstrated 112 bouts of pruritus. Scratches induced by the histamine-free vehicle PBS (not shown in Table 5) served as control (6±3 bouts of scratching; N=8)

This test used histamine to induce pruritus. Histamine H-1 and H-4 receptors express constitutive activity and the H-1 and H-4 receptor signaling does not require the availability of free histamine. The histamine inhibitors are "inverse agonists" at both receptor types. The constitutive histamine receptors are known to be up-regulated during inflammation. The results from this study are shown in Table 5.

TABLE 5

Antipruritic activity in mice; oral administration.

| Test Article | N | Bouts/40 min Mean ± SEM | Bouts as % of Vehicle Controls |
|---|---|---|---|
| Vehicle for NORK, DES and OCLA | 9 | 92.0 ± 15.3 | 100 |
| Norketotifen 1 mg/kg | 7 | 84.7 ± 11.6 | 92 |
| Norketotifen 3 mg/kg | 7 | 34.1 ± 9.6 | 37** |
| Norketotifen 10 mg/kg | 6 | 17.8 ± 3.1 | 19** |
| Norketotifen 100 mg/kg | 8 | 8.3 ± 2.8 | 9*** |
| Desloratadine 20 mg/kg | 7 | 112.0 ± 14.5 | 122 |
| Oclacitinib 20 mg/kg | 8 | 50.9 ± 18.7 | 55* |
| J&J7777120 20 mg/kg | 8 | 63.6 ± 11.7 | 57* |
| Vehicle for JNJ7777120 | 8 | 112.0 ± 14.3 | (100) |

*means P ≤ 0.05
**means P ≤ 0.01
***means P ≤ 0.001
NORK = norketotifen
DES = desloratadine
OCLA = oclacitinib Example 6

Sedative Effects in Mice

The sedation study in mice has previously been used by Schering in the loratadine project (U.S. Pat. No. 4,659,716, 1987) and by Sepracor in the desloratadine project (U.S. Pat. No. 5,595,997), which patents are hereby included by reference for their disclosure of sedation studies. In short, physostigmine (1.0 mg/kg to 2.0 mg/kg, s.c.) generally results in 100% lethality when given to groups of mice (10 mice /group) transferred into a small volume of space. Mice administered a sedating drug prior to the physostigmine injection are protected from the stress and survive. In the present study, test compounds were given orally 60 minutes prior to physostigmine injection. The number of surviving (sedated) mice was counted 30 minutes after injection of the physostigmine dose. Results are shown from tests that were performed between the years 1997 and 2009 in Table 6.

TABLE 6

Sedative effects in mice

|  | Oral dose (mg/kg) | Sedated animals |
|---|---|---|
| VEHICLE | — | 0/10 |
| NORKETOTIFEN | 83 | 3/10 |
| NORKETOTIFEN | 100 | 3/10 |
| NORKETOTIFEN | 150 | 3/10 |
| NORKETOTIFEN | 180 | 6/10 |
| S-NORKETOTIFEN | 100 | 0/10 |
| S-NORKETOTIFEN | 150 | 0/10 |
| R-NORKETOTIFEN | 100 | 3/10 |
| R-NORKETOTIFEN | 150 | 3/10 |
| KETOTIFEN (Zaditen ®; Gen-1) | 25 | 5/10 |
| KETOTIFEN (Zaditen ®; Gen-1) | 50 | 8/10 |
| KETOTIFEN (Zaditen ®; Gen-1) | 100 | 10/10 |
| CYPROHEPTADINE (Periactin ®; Gen-1) | 100 | 9/10 |
| PYRILAMINE (Mepyramine ®; Gen-1) | 100 | 8/10 |
| HYDROXYZINE (Atarax ®; Gen-1) | 100 | 9/10 |
| DIPHENHYDRAMINE (Benadryl ®; Gen-1) | 50 | 5/10 |
| DIPHENHYDRAMINE (Benadryl ®; Gen-1) | 100 | 8/10 |
| ASTEMIZOLE (Hismanal ®; Gen-2) | 100 | 1/10 |
| NORASTEMIZOLE (Soltara ™; Gen-2) | 100 | 0/10 |
| LORATADINE (Claritin ®; Gen-2) | 150 | 1/10 |
| DESLORATADINE (Clarinex ®; Gen-2) | 150 | 0/10 |
| TERFENADINE (Seldane ®; Gen-2) | 150 | 0/10 |
| FEXOFENADINE (Allegra ®; Gen-2) | 150 | 0/10 |

Gen-1 = Generation-1 (sedating antihistamines)
Gen-2 = Generation-2 (non-sedating antihistamines)

Results: All registered Generation-1 antihistamines were sedating in mice and all registered Generation-2 antihistamines were free from sedation, using the physostigmine lethality test. This test system has therefore been considered to be highly reliable in differentiation between sedative and non-sedative antihistaminic compounds. Racemic norketotifen expressed sedative activity in this test system.

Example 7

Sedative Effects in Humans

Sedation studies were performed in human volunteers, where the volunteers were administered norketotifen orally at doses of 5 mg or 10 mg (o.d. and b.i.d. for one to four days), which is believed to be about a 10-fold and 20-fold, respectively, higher dose than the amount of norketotifen formed as a metabolite after a clinical dose of ketotifen 1.0 mg. The test articles were administered in gelatin capsules and vehicle-capsules were empty. The volunteers were dosed at 8-10 AM and had been fasted overnight before dosing. All observations regarding sedation/sleepiness were made by the individual volunteers and by a scientist with previous experience in human CNS-studies. As a positive control, ketotifen was administered as a single oral dose of 2 mg to the volunteers (two tablets Zaditen®, Paladin, each tablet containing 1 mg ketotifen). All test articles were in the form of hydrogen fumarate salts.

The test results demonstrated complete lack of sedation in all volunteers who had been administered racemic norketotifen at oral doses of 5 mg or 10 mg (o.d. or bid for up to four days. The test results also demonstrated that ketotifen caused sedation in the human volunteers, which is not surprising, since sedation/drowsiness is a dose-dependent and dose-limiting side effect of ketotifen. As understood by those skilled in medical sciences, lack of sedation of RS-norketotifen in humans implies lack of sedation of both S- and R-norketotifen in humans.

Humans are known to express sedation within one hour after a single oral dose of Generation-1 antihistamines, such as for example diphenhydramine (Benadryl®, McNeill) or ketotifen (Zaditen®, Novartis). The test article was therefore usually administered for one day only, although some experiments were performed with the test article being administered for three consecutive days.

Surprisingly, norketotifen did not cause sedation in the human volunteers, which is contrary to the results from earlier animal studies using the mouse physostigmine model (Example 6), which had been considered to be of high predictive value. To our knowledge, this is the first study that has been performed to specifically study sedative side effects of RS-norketotifen in humans and it has now surprisingly been found that racemic norketotifen is completely free from sedative effects in humans, even after administration of high oral doses.

Example 8

Toxicological Effects

Acute toxicological studies were performed in rats (Sprague-Dawley; M and F; 200-250 grams). The animal-sparing Up-and-Down Procedure, recommended by FDA and OECD, was used. Both oral and intravenous toxicity tests were performed.

The acute toxicity, expressed as estimated LD50 and calculated in mg/kg body weight of norketotifen and ketotifen are shown in Table 7. Both compounds were administered as hydrogen fumarate salts.

Results: Norketotifen is significantly less toxic than ketotifen after intravenous administration and after oral administration.

TABLE 7

Toxicological effects

| | Acute toxicity (estimated LD50) mg/kg | |
|---|---|---|
| TEST SYSTEM | NORKETOTIFEN | KETOTIFEN |
| RAT; intravenous | 10-15 | 5-10 |
| RAT; oral | 1500-2000 | <300 |

Example 9

Anti-inflammatory Effects in vivo. Topical Drug Administration

In order to investigate the effects of topical administration of the test compounds in dermal inflammation, a modified croton oil model was used. About 10 mg of a cream containing 1.0% norketotifen or a vehicle cream was applied to both ears of mice for 30 minutes. The cream was then removed and a solution of 1% croton oil in 20 µl acetone was applied to both ears. After the acetone had dried (10 seconds), the cream containing the test article (or vehicle) was reapplied and the animals were returned to their cages. At 0, 30, 60 and 90 minutes following the croton oil administration, groups of four animals were anesthetized with halothane and euthanized. Cream was wiped from the ears and ears were removed and weighed.

The effects of 10 mg of a cream containing 1.0 percent RS-norketotifen at 30, 60 and 90 minutes after administration of test articles are shown in the following table 8. All results represent mean ear weights (±S.E.M.) from 8 ears.

TABLE 8

Anti-inflammatory effects of norketotifen in vivo after dermal application

| Time after Croton Oil Application (min) | Average Ear Weight (mg) ± S.E.M | |
|---|---|---|
| | Vehicle | RS-Norketotifen |
| 0 (predose) | 35 ± 1 | 36 ± 1 |
| 30 | 41 ± 1 | 36 ± 1 |
| 60 | 41 ± 1 | 37 ± 2 |
| 90 | 46 ± 2 | 36 ± 2 |

In this study, the test article (racemic norketotifen) was applied topically to the ears of mice in the concentration 1.0 percent. A cream containing 1.0 percent (w/w) of norketotifen completely inhibited the pro-inflammatory of topically applied croton oil.

Since a cream containing 1.0 percent norketotifen completely inhibited the inflammation, it was concluded that the concentration of norketotifen in topical formulations could be further decreased to 0.1 percent.

Example 10

Antipruritic Effects in vivo. Topical Drug Administration

Antipruritic effects were tested in vivo in CD-1 female mice aged 10-12 weeks, according to methods known in the art. The hair was clipped over the rostral part of the back at the interscapular level of the mice one day before dosing. Before testing, the mice were placed in individual clear plastic cages for at least one hour for acclimation. The animals were dosed topically by applying to the skin, the formulated cream, containing 1.0% RS-norketotifen.

In preparing 1% creams, the free base of RS-norketotifen was dissolved in ethanol, resulting in a 2.5% solution. Lanolin was weighed and liquified by submerging the vessel containing lanolin in hot water. While the lanolin was liquid, it was rapidly nixed (by vortexing) with the 2.5% norketotifen solution in ethanol, resulting in a 1.0 percent solution. The ethanol/lanolin solution was allowed to solidify, resulting in a cream which consisted of 1.0% RS-norketotifen in 60% lanolin/40% ethanol. A cream containing 60% lanolin/40% ethanol served as control. Sixty minutes after the topical application of the cream, an intradermal injection of histamine (300 nmol in 20 µl phosphate buffered saline (PBS), pH 7.4) was administered into the clipped area. Immediately after the histamine injection, the bouts of scratches by the mice were counted for 40 minutes. Test results are shown in Table 9.

TABLE 9

Effects of norketotifen cream on histamine-induced pruritus in mice.

| Test Article | N | Bouts/40 min | Bouts as % of Vehicle Controls |
|---|---|---|---|
| Cream (vehicle) | 8 | 144 ± 16 | 100 |
| Cream w. NORK 10 mg/ml | 8 | 61 ± 9 | 42** |

**means P ≤ 0.01
NORK = norketotifen

From these results, it can be concluded that a single topical application of a cream containing 1.0 percent RS-norketotifen reduced the histamine-induced pruritus in mice by 58% when compared with the Vehicle Control. It was concluded that since a concentration of 1.0 percent of norketotifen offered 58 percent inhibition within a short time of dermal application, the concentration of norketotifen in topical formulations for clinical use can be further decreased to 0.1 percent.

Example 11

Antimicrobial Tests of Norketotifen

Several studies have been performed to evaluate possible antimicrobial activities of norketotifen. Shown here are the results from a standard microbiological test, where the results are expressed as MIC (Minimal Inhibitory Concentration) of the test article against selected exemplary dermal bacteria (such as for example *Staphylococcus aureus*) and dermal fungi (such as for example *Malassezia* sp) that are commonly found in human with dermal diseases. Tests of the antimicrobial activities of norketotifen against other fungi and other bacteria, such as for example the fungi *Candida albicans* and *Malassezia pachydermatis* and the bacterium *Helicobacter pylori* have demonstrated potent antimicrobial activities of norketotifen. All the MIC-tests shown in Table 10 were performed in duplicates, using 10 concentrations of the test articles. The Initial Numbers Controls had to demonstrate ≥1×10 4 CFU/ml (CFU=Colony Forming Units) for each test microorganism. The test culture tubes/plates were incubated in temperatures and durations appropriate for each microorganism (*S. aureus*: 36° C. and 24 hours; *M. globosa*: 30° C. and 24 hours). Results from tests with the bacterium *Staphylococcus aureus* and the fungus *Malassezia globosa* are shown in Table 10.

TABLE 10

Antimicrobial activities of norketotifen

| Test Article | S. aureus* MIC (mg/ml) | M. globosa MIC (mg/ml) |
|---|---|---|
| RS-norketotifen HF | 0.5 | 0.25 |
| R-norketotifen HF | 1.0 | 0.5 |
| S-norketotifen HF | 0.5 | 0.25 |

*Methicillin-resistant *S. aureus* (MRSA) or non-resistant *S. aureus*.

The results indicate that topical (dermal) compositions containing 1.0% (10 mg/ml) of norketotifen (or an isomer thereof) express significant antimicrobial efficacy, particularly when applied to the skin of patients suffering from atopic dermatitis, psoriasis and other dermal diseases, where the epidermal barriers are severely malfunctioning.

Example 12

Exemplary Oral Dosage Formulation

The active ingredient is blended with the lactose and cellulose until a uniform blend is formed. The blue lake is added and further blended. Finally, the calcium stearate is blended in, and the resulting mixture is compressed into tablets using for example a 9/32-inch (7 mm) shallow concave punch. Tablets of other strengths may be prepared by altering the ratio of active ingredient to the excipients or to the final weight of the tablet. Those skilled in the art realize that oral formulations can also be in the form of for example a capsule or a liquid formulation.

TABLE 11

Tablet formulations

| Ingredient | Amount per tablet | Amount per batch |
| --- | --- | --- |
| Norketotifen | 40 mg | 400 g |
| Microcrystalline cellulose | 30 mg | 300 g |
| Lactose | 70 mg | 700 g |
| Calcium stearate | 2 mg | 20 g |
| FD&C Blue #1 Lake | 0.03 mg | 300 |

Example 13

Exemplary Topical (Dermal) Formulations

Examples of topical (dermal) solutions, ointments, emulsions and creams are shown in Tables 12-18.

TABLE 12

Examples of topical solutions formulations containing norketotifen

| | Excipients in per cent | | |
| --- | --- | --- | --- |
| | 1008 | 1009 | S1010 |
| Norketotifen HF (%) | 0.2 | 0.2 | 0.2 |
| Sodium phosphate dibasic | 0.473 | — | 0.160 |
| Sodium phosphate monobasic, monohydrate | 0.460 | — | — |
| NaCl | 0.480 | — | — |
| Sodium citrate | — | 0.300 | — |
| Propylene glycol | — | 1.750 | — |
| Methylcellulose | — | — | 0.500 |
| Glycerin | — | — | 2.400 |
| Water | q.s. | q.s. | q.s. |
| pH | 4.6-6.2 | 4.6-6.2 | 4.6-6.2 |

Norketotifen HF = norketotifen hydrogen fumarate

If needed, the viscosity can be adjusted by a viscosity-modifying agent to obtain the preferred viscosity. The final acidity can be adjusted by adjusting the concentrations of the buffering agents or by adding an acid or a base.

The solution formulations were prepared by adding the excipients, one at a time to an appropriate amount of water, followed by mixing until dissolved. Once all excipients had been added and dissolved, norketotifen was added to the solution of excipients and mixed continuously until dissolved. The acidity of the solutions was measured and adjusted by modifying the buffer system or by adding an acid or a base solution to the desired pH. If needed, viscosity and tonicity were adjusted as indicated.

TABLE 13

An example of hydrophilic ointments/gels containing norketotifen

| | Batch G1009 |
| --- | --- |
| Norketotifen HF (%) | 1.0 |
| PEG 300 (%) | 69.0 |
| PEG 3350 (%) | 30.0 |

The solubility of norketotifen was significantly increased in certain formulations, such as gels and ointments where the solvents were not water. Thus, the solubility of norketotifen was about 1.0 percent in formulation G1009 (Table 13), where the solvent was a mixture of two polyethylene glycols.

The composition of Table 13 was prepared by mixing the two polyethylene glycols in a suitable container and heating to 60-65° C. This heating step melts the high molecular weight polyethylene glycol. Next, norketotifen was added and the composition was mixed until the active ingredient was dissolved. Finally, the composition was cooled with mixing to allow the ointment/gel to thicken. The viscosity was 30,000 cP or greater. The pH range for these compositions was not measured since the formulations were non-aqueous. If needed, the tonicity can be adjusted by adding a tonicity-adjusting agent to obtain the preferred tonicity.

TABLE 14

An example of hydrophobic ointments/gels containing norketotifen

| | Batch G1012 |
| --- | --- |
| Norketotifen HF (%) | 1.0 |
| Propylene glycol (%) | 10.0 |
| Glyceryl stearate (%) | 0.5 |
| Cetyl alcohol (%) | 0.5 |
| White petrolatum | q.s. |

Batch G1012 contained propylene glycol as a solvent for norketotifen, glycerol stearate and cetyl alcohol as surfactants and white petrolatum as base.

The hydrophobic ointment was prepared by dissolving norketotifen in propylene glycol. The solubility of norketotifen was about 1.0 percent in propylene glycol. Next, glyceryl stearate, cetyl alcohol, and white petrolatum were added to a suitable container and heated to 65-70° C. This heating step melts the surfactants and the petrolatum. Next, norketotifen solution was slowly added and the composition mixed until the solvent was dispersed. Finally, the composition was cooled with mixing to allow the ointment to thicken. If needed, acidity can be adjusted by adding an acid solution or a base solution to obtain the preferred acidity. If needed, viscosity can be adjusted with a viscosity-modifying agent to obtain the preferred viscosity.

TABLE 15

Examples of topical emulsions containing norketotifen

| | ED1012b | ED1015b |
| --- | --- | --- |
| Norketotifen HF (%) | 1.0 | 1.0 |
| Sodium phosphate dibasic (%) | 0.160 | 0.160 |
| Propylene glycol (%) | 1.850 | 1.850 |
| Castor oil (%) | 1.250 | 1.250 |
| Polyoxyl 35 castor oil (%) | 1.000 | 1.000 |
| Methylcellulose (%) | 0.200 | — |
| 1.0N HCl or | q.s. to | q.s. to |
| 1.0N NaOH (%) | target pH | target pH |

TABLE 15-continued

Examples of topical emulsions containing norketotifen

|  | ED1012b | ED1015b |
|---|---|---|
| Water | q.s. (2) | q.s. (2) |
| pH | 5 to 7 | 5 to 7 |

The batches ED1012b and ED1015b contained a phosphate buffer, propylene glycol as solvent/moisturizer/tonicity modifier, parabens as preservatives, castor oil and polyoxyl castor oil as surfactants and methylcellulose (if used) as a stabilizer/viscosity modifier. Emulsions containing norketotifen can be used at pH of about 5.0 to about 7.0.

The selected emulsions in Table 15 were prepared by adding propylene glycol, castor oil, ethoxylated castor oil, and water to a suitable container. The contents of the container were sonicated with a ½" ultrasonic probe (Sonics Inc. Vibra Cell) for 20 minutes. The resulting emulsion droplets were mostly less than 0.5 microns. The emulsion was filtered through a 0.22-micron cellulose acetate filter. After filtration, norketotifen and buffer salts were added. The viscosity of norketotifen emulsions can be adjusted by a compatible viscosity-modifying agent.

TABLE 16

An example of topical liposome compositions containing norketotifen

|  | LIP1011 |
|---|---|
| Norketotifen HF (%) | 1.0 |
| Sodium phosphate dibasic (%) | 0.16 |
| Glycerin (%) | 2.40 |
| Soy lecithin (%) | 1.00 |
| Cholesterol (%) | 0.05 |
| Water | q.s. |

Topical liposome compositions were made, comprising norketotifen at concentrations preferably between 1.0 percent and 10.0 percent. The liposome compositions were having a preferred viscosity that ranged from 1.000 to 200,000 cP. Topical liposome compositions have pH of 4 to 7, preferably pH 5.2 to 6.2. The liposome compositions are approximately iso-osmotic. Said emulsions also contained excipients, such as humectants, viscosity modifying agents, tonicity agents, chelating agents, buffers, surfactants, mucoadhesives and antioxidants. Said liposome emulsions were designed for once-daily dermal administration or for repeated dermal administrations from two to five times daily to a mammal in need thereof.

Incorporating norketotifen in a selected liposome composition will enhance residence time in the skin and improve drug delivery to the tissues. An exemplary liposome composition containing norketotifen is shown in Table 16. The acidity can be changed by adjustment of the buffer or by adding an acid or a base as known to those skilled in the art.

TABLE 17

An example of a dermal suspension containing norketotifen

|  | SUS1011 |
|---|---|
| Norketotifen FB (%) | 5.0 |
| Poloxamer 407 | 0.6 |
| Boric acid | 0.2 |

TABLE 17-continued

An example of a dermal suspension containing norketotifen

|  | SUS1011 |
|---|---|
| Sodium chloride | 0.2 |
| Water | q.s. |
| pH | 5.0 to 7.0 |

Norketotifen FB = norketotifen free base

Both norketotifen salts and norketotifen FB can be formulated as suspensions. Several experiments were done and acidity was adjusted over a wide range. It was determined that emulsions can be used at pH of about 5.0 to about 7.0. An example of a preferred suspension containing norketotifen free base is shown in Table 17, where all percent are w/w. Viscosity will be adjusted by addition of one or more viscosity-modifying agents, which will offer stability to the suspensions.

TABLE 18

An example of a dermal cream containing norketotifen

|  | PT 112706 |
|---|---|
| Norketotifen FB (%) | 1.0 |
| Ethanol (%) | 39.0 |
| Lanolin (%) | 60.0 |
| Surfactant(s) (%) | (0.2) |
| Antioxidant(s) (%) | (0.2) |

Both norketotifen salts and norketotifen free base can be formulated as creams. An example of a cream containing norketotifen free base is shown in Table 18, where all percent are w/w.

In preparing creams containing 1 percent of the free base of norketotifen, the active ingredient was dissolved in ethanol, resulting in a 2.5 percent solution. Lanolin was weighed and liquefied by submerging the vessel containing lanolin in hot water. While the lanolin was a liquid, it was rapidly mixed (by vortexing) with the 2.5% norketotifen solution in ethanol to result in a 1.0 solution. The ethanol/lanolin solution was allowed to cool off and solidify, resulting in a cream which consisted of 1 percent norketotifen in the lanolin/ethanol cream, which will be kept in a closed tube to avoid evaporation. To improve shelf-life, a surfactant (such as for example glyceryl stearate, 0.1 to 0.3 percent) and an antioxidant (such as for example ascorbic acid, 0.1 to 0.3 percent) can optionally be added, as shown in Table 18.

Dosage forms for topical (dermal) application may be prepared for example as solutions (Table 12), as hydrophilic ointments (Table 13), as hydrophobic ointments (Table 14), as emulsions (Table 15), as liposome compositions (Table 16), as suspensions (Table 17), and as creams (Table 18). The dermal compositions may also contain additional excipients, and a large number of excipients have been tested for compatibility with norketotifen. Dermal composition may contain one or more active compounds and the compounds may be prepared as bases or salts. Dermal composition may be applied to the skin under occlusive dressing or as a constituent of a dermal delivery system ("patch," etc.)

As used herein, the terms "pharmaceutically acceptable salts" or "a pharmaceutically acceptable salt thereof" refer to norketotifen salts, which have been prepared from pharmaceutically acceptable non-toxic acids. Exemplary pharmaceutically acceptable acid as for the compound of the present invention include acetic, benzenesulfonic (besylate), benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pathothenic, phosphoric, p-toluenesulfonic, succinic, sulfuric, tartaric, and the like. The hydrochloride salt and the hydrogen fumarate salt are particularly preferred.

The term "topical" (as for example "topical treatment") as used herein is synonymous to the term "dermal" (as for example "dermal treatment".) The term "dermal" (as for example "dermal infection") as used herein is synonymous to the term "skin" (as for example "skin infection".) The term "antimicrobial" as used herein refers to antibacterial, antifungal and antiviral activities or effects. The term "formulation" (as for example "dermal formulation") as used herein is synonymous to the term "composition" (as for example "dermal composition").

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted.

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A method of treating skin infections in a human patient suffering from a skin infection, consisting of topically administering a topical formulation to skin of a human patient that is infected with a bacterium or a fungus, wherein the topical formulation consists of a therapeutically effective amount of RS-norketotifen or a pharmaceutically acceptable salt thereof and a pharmaceutically acceptable excipient,
    wherein the topically applied RS-norketotifen or pharmaceutically acceptable salt thereof inhibits the growth of the bacterium or fungus, and
    wherein the RS-norketotifen or pharmaceutically acceptable salt thereof is the only active antimicrobial agent in the topical formulation.

2. The method of claim 1, wherein the infection is a fungal infection.

3. The method of claim 2, wherein the fungus is a *Malassezia* sp.

4. The method of claim 3, wherein the fungus is *Malassezia globosa*.

5. The method of claim 2, wherein the fungus is *Candida albicans*.

6. The method of claim 1, wherein the infection is a bacterial infection.

7. The method of claim 6, wherein the bacterium is a *Staphylococcus* sp.

8. The method of claim 7, wherein the bacterium is *Staphylococcus aureus*.

9. The method of claim 1, wherein the topical formulation contains RS-norketotifen or a salt thereof at a concentration of 0.1 percent to 10.0 percent by weight.

* * * * *